United States Patent
Rosomoff

(10) Patent No.: US 12,087,420 B2
(45) Date of Patent: *Sep. 10, 2024

(54) DYNAMIC USER INTERFACE GENERATION FOR DELIVERY SCHEDULING OPTIMIZATION

(71) Applicant: Express Scripts Strategic Development, Inc., St. Louis, MO (US)

(72) Inventor: Peter Andrew Rosomoff, Wildwood, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/994,609

(22) Filed: Nov. 28, 2022

(65) Prior Publication Data
US 2023/0099084 A1    Mar. 30, 2023

Related U.S. Application Data

(63) Continuation of application No. 16/449,317, filed on Jun. 21, 2019, now Pat. No. 11,515,023.

(51) Int. Cl.
G16H 20/10    (2018.01)
G06Q 10/083    (2024.01)
G06Q 10/1093    (2023.01)

(52) U.S. Cl.
CPC ........... *G16H 20/10* (2018.01); *G06Q 10/083* (2013.01); *G06Q 10/1097* (2013.01)

(58) Field of Classification Search
CPC ........ G16H 20/10; G16H 10/60; G16H 40/67; G16H 70/40; G06Q 10/083; G06Q 10/1097

(Continued)

(56) References Cited

U.S. PATENT DOCUMENTS 5,839,117 A    11/1998    Cameron
8,073,723 B1    12/2011    Bilibin
(Continued)

FOREIGN PATENT DOCUMENTS

CA    2836162 A1    6/2015
EP    1471454 A2 *    10/2004    ........... G06F 19/326
(Continued)

OTHER PUBLICATIONS

Eldar-Lissai, Ad; The effect of direct-to-consumer prescription drug advertising on geographic variations of medical care ; University of Rochester. ProQuest Dissertations Publishing, 2010. 3414011. (Year: 2010).*

(Continued)

*Primary Examiner* — Hiep V Nguyen
(74) *Attorney, Agent, or Firm* — Miller Johnson

(57) ABSTRACT

A system for generating dynamic user interfaces includes memory hardware storing instructions and processor hardware executing the instructions. The instructions include generating an interactive graphical user interface with fields corresponding to dates. The instructions include generating a selectable user interface element at a first field corresponding to a scheduled delivery date for a recipient. The instructions include, in response to a user dragging-and-dropping the selectable user interface element to a second field corresponding to an adjusted delivery date for the recipient, calculating a supply measure of a prior fill remaining with the recipient based on a stated duration of the prior fill and a date indicating receipt of the prior fill by the recipient. The instructions include, in response to the supply measure being greater than the threshold, moving the selectable user interface element to the second field and updating the scheduled delivery date to be the adjusted delivery date.

20 Claims, 20 Drawing Sheets

(58) Field of Classification Search
USPC .......................................................... 705/2
See application file for complete search history.

(56) References Cited

U.S. PATENT DOCUMENTS

| | | | |
|---|---|---|---|
| 8,311,513 B1 | 11/2012 | Nasserbakht | |
| 8,429,019 B1 | 4/2013 | Yeatts | |
| 8,498,883 B2 | 7/2013 | Lorsch | |
| 8,560,347 B1* | 10/2013 | Ali | G06Q 10/00 |
| | | | 705/2 |
| 8,949,244 B2 | 2/2015 | Porter | |
| 8,949,738 B2 | 2/2015 | Felt | |
| 9,703,826 B2 | 7/2017 | Yerkes | |
| 10,043,206 B2 | 8/2018 | Zamer | |
| 10,572,630 B1* | 2/2020 | Schmeling | G06Q 10/1093 |
| 2002/0082865 A1 | 6/2002 | Bianco | |
| 2004/0199412 A1 | 10/2004 | McCauley | |
| 2005/0149362 A1 | 7/2005 | Peterson | |
| 2007/0198296 A1 | 8/2007 | Pellinat | |
| 2007/0238936 A1 | 10/2007 | Becker | |
| 2008/0077439 A1 | 3/2008 | Guion | |
| 2008/0313005 A1 | 12/2008 | Nessland | |
| 2009/0037223 A1 | 2/2009 | Green | |
| 2009/0164236 A1 | 6/2009 | Gounares | |
| 2009/0234707 A1 | 9/2009 | Perez | |
| 2011/0082705 A1 | 4/2011 | Kobylevsky | |
| 2012/0162265 A1* | 6/2012 | Heinrich | G06F 3/04883 |
| | | | 345/173 |
| 2012/0253868 A1 | 10/2012 | Ach | |
| 2013/0325541 A1 | 12/2013 | Capriotti | |
| 2014/0156298 A1 | 6/2014 | Crawford | |
| 2014/0351028 A1 | 11/2014 | Killoh | |
| 2015/0058035 A1* | 2/2015 | Ayshford | G16H 40/20 |
| | | | 705/2 |
| 2015/0213631 A1* | 7/2015 | Vander Broek | G06Q 30/02 |
| | | | 345/589 |
| 2016/0350721 A1* | 12/2016 | Comerford | H04L 67/306 |
| 2016/0371620 A1 | 12/2016 | Nascenzi | |
| 2017/0004281 A1 | 1/2017 | Hartman-Tinder | |
| 2017/0116384 A1 | 4/2017 | Ghani | |
| 2017/0316370 A1 | 11/2017 | Putcha | |
| 2018/0150611 A1 | 5/2018 | Hasan | |

FOREIGN PATENT DOCUMENTS

| | | |
|---|---|---|
| WO | 2015013694 A2 | 1/2015 |
| WO | 2015035309 A1 | 3/2015 |
| WO | 2017027974 A1 | 2/2017 |

OTHER PUBLICATIONS

Amazon, Subscribe & Save, https://www.amazon.com/b/ref=rcxsubs_details?ie=UTF8&node=15283820011, as early as Sep. 7, 2018.
Carezone Medical, https://play.google.com/store/apps/details?id=com.carezone.caredroid.careapp.medications&hl=en, Aug. 21, 2018.
Cronofy, A New Way To Schedule Medical Appointments, https://www.cronofy.com/medical-appointment-scheduling-software/. as early as Sep. 7, 2018.
docmein.com, https://www.getapp.com/healthcare-pharmaceuticals-software/a/docmein/, as early as Sep. 7, 2018.
Q-NOMY, Medical Appointment Scheduling, https://www.qnomy.com/medical-appointment-scheduling, 2014.
Selecthub, Streamline Patient Scheduling with These Software Solutions, https://selecthub.com/medical-software/patient-scheduling-software-solutions/, as early as Sep. 7, 2018.
Wpdevelop, Oplugins, Booking Calendar, https://wordpress.org/plugins/booking/, as early as Sep. 7, 2018.
Karimi, Elnaz; Integrative Predictive Support Systems for Hospital's Resource Planning and Scheduling; Ecole Polytechnique, Montreal (Canada). ProQuest Dissertations Publishing, 2018. 27537028 (Year: 2018).

* cited by examiner

OCTOBER

| MON | TUE | WED | THU | FRI |
|---|---|---|---|---|
| 1 | 2 | 3 | 4 | 5 |
| 8 | 9 | 10 | 11 | 12 |
| 15 | 16 | 17 | 18 | 19 |
| 22 | 23 | 24 | ☆ JANUVIA SCHEDULED (25) | 26 |
| 29 | 30 | 31 | 1 | 2 |

402-3

NOVEMBER

| MON | TUE | WED | THU | FRI |
|---|---|---|---|---|
| 29 | 30 | 31 | 1 | ☆ VIT D-2 SCHEDULED (2) |
| 5 | 6 | 7 | 8 | 9 |
| 12 | 13 | 14 | 15 | 16 |
| 19 | 20 | ♡ ZOFRAN SCHEDULED (21) | 22 | 23 |
| ☆ BYDUREON SCHEDULED (26) | ☆ ATORVASTATIN SCHEDULED (27) | 28 | 29 | 30 |

YOUR SCHEDULE OF DELIVERIES
SELECT SPECIFIC FAMILY MEMBERS OR PRESCRIPTIONS TO VIEW BY CLICKING ON THEM (CLICK "CLEAR SELECTIONS" BUTTON TO SEE ALL)

☆ JOHN | ◇ JANE | △ BILLY | ◇ ALICE

☆ JANUVIA | ☆ PIOGLITAZONE | ☆ VI: D-2 | ☆ ATORVASTATIN
☆ BYDUREON | ◇ LISINOPRIL | ◇ ZOFRAN

440 →
416 →
[OPTIMIZE MY SCHEDULE]
[CUSTOMIZE MY VIEW]
[CLEAR SELECTIONS]

[TODAY] [<] [>]

2018  [YEAR] [MONTH] [WEEK] [DAY]

AUG

| MON | TUE | WED | THU | FRI |
|---|---|---|---|---|
| 30 | 31 | 1 | 2 | 3 |
| 6 | 7 | 8 | 9 | 10 |
| 13 | 14 | 15 | 16 | 17 |
| 20 | 21 | 22 | 23 | 24 |
| 27 | 28 | ☆ JANUVIA SCHEDULED 29 | 30 | 31 |

SEPT

| MON | TUE | WED | THU | FRI |
|---|---|---|---|---|
| 27 | 28 | 29 | 30 | 31 |
| ☆ PIOGLITAZONE RENEWAL —442 / ☆ VIT D-2 SCHEDULED 3 | 4 | 5 | 6 | 7 |
| 10 | 11 | 12 | 13 | 14 |
| 17 | 18 | 19 | 20 | ♡ ZOFRAN SCHEDULED / ☆ ATORVASTATIN SCHEDULED / ☆ BYDUREON SCHEDULED 21 —444 |
| 24 | 25 | 26 | 27 | 28 |

YOUR SCHEDULE OF DELIVERIES
SELECT SPECIFIC FAMILY MEMBERS OR PRESCRIPTIONS TO VIEW BY CLICKING
ON THEM.(CLICK"CLEAR SELECTIONS" BUTTON TO SEE ALL)

☆ JOHN  ◇ JANE  △ BILLY  ◇ ALICE

☆ JANUVIA  ☆ PIOGLITAZONE  ☆ VIT. D-2  ☆ ATORVASTATIN
☆ BYDUREON  ◇ LISINOPRIL  ◇ ZOFRAN

450 →

[OPTIMIZE MY SCHEDULE]
[CUSTOMIZE MY VIEW]
[CLEAR SELECTIONS]

[<][>] [TODAY]  2018  [YEAR][MONTH][WEEK][DAY]

| AUG | | | | | | SEPT | | | | |
|---|---|---|---|---|---|---|---|---|---|---|
| MON | TUE | WED | THU | FRI | | MON | TUE | WED | THU | FRI |
| 30 | 31 | 1 | 2 | 3 | | 27 | 28 | 29 | 30 | 31 |
| 6 | 7 | 8 | 9 | 10 | | ☆ PIOGLITAZONE RENEWAL 3 | 4 | 5 | 6 | 7 |
| 13 | 14 | 15 | 16 | 17 | | ☆ VIT D-2 SCHEDULED 10 | 11 | 12 | 13 | 14 |
| 20 | 21 | 22 | 23 | 24 | | 17 | 18 | 19 | 20 | ☆ ZOFRAN SCHEDULED / ☆ ATORVASTATIN SCHEDULED / ☆ BYDUREON SCHEDULED 21 |
| 27 | 28 | 29 ☆ JANUVIA BEING DELIVERED | 30 | 31 | | 24 | 25 | 26 | 27 | 28 |

RESCHEDULED DELIVERIES NOT GUARANTEED — 452

OCTOBER

| MON | TUE | WED | THU | FRI |
|---|---|---|---|---|
| 1 | 2 | 3 | 4 — 462 | 5 ☆ JANUVIA SCHEDULED |
| 8 | 9 | 10 | 11 | 12 |
| 15 | 16 | 17 | 18 | 19 |
| 22 | 23 | 24 | 25 ☆ JANUVIA | 26 |
| 29 | 30 | 31 | 1 | 2 |

NOVEMBER

| MON | TUE | WED | THU | FRI |
|---|---|---|---|---|
| 29 | 30 | 31 | 1 | 2 ☆ VIT D-2 SCHEDULED |
| 5 | 6 | 7 | 8 | 9 |
| 12 | 13 | 14 | 15 | 16 |
| 19 | 20 | 21 ♡ ZOFRAN SCHEDULED / ☆ ATORVASTATIN SCHEDULED / ☆ BYDUREON SCHEDULED | 22 | 23 |
| 26 | 27 | 28 | 29 | 30 |

470 →

YOUR SCHEDULE OF DELIVERIES
SELECT SPECIFIC FAMILY MEMBERS OR PRESCRIPTIONS TO VIEW BY CLICKING
ON THEM (CLICK "CLEAR SELECTIONS" BUTTON TO SEE ALL)

☆ JOHN | ♡ JANE | △ BILLY | ◇ ALICE

☆ JANUVIA | ☆ PIOGLITAZONE | ☆ VI: D-2 | ☆ ATORVASTATIN
☆ BYDUREON | ♡ LISINOPRIL | ♡ ZOFRAN

[OPTIMIZE MY SCHEDULE]
[CUSTOMIZE MY VIEW]
[CLEAR SELECTIONS]

[TODAY] [<] [>]   2018  472   [YEAR] [MONTH] [WEEK] [DAY]

| | AUG | | | | | |
|---|---|---|---|---|---|---|
| MON | TUE | WED | THU | | | FRI |
| 30 | 31 | 1 | | | | |
| 6 | 7 | 8 | | | | |
| 13 | 14 | 15 | 16 | 17 | | |
| 20 | 21 | 22 | 23 | | | |
| 27 | 28 | ☆ JANUVIA SCHEDULED 29 | 30 | 31 | | |

(Week row with Pioglitazone Renewal / Vit D-2 Scheduled on day 10; Thu 30, Fri 31)

Notification dialog:
NOTIFICATION
JANUVIA TABS 50MG WAS MOVED TO 2018-10-05, ARE
YOU SURE ABOUT THIS CHANGE ?
[OK]  [CANCEL]

Additional week: 6, 7; 13, 14; 19, 20 (♡ ZOFRAN SCHEDULED, ☆ ATORVASTATIN SCHEDULED, ☆ BYDUREON SCHEDULED) 21; 26, 27, 28

OCTOBER

| MON | TUE | WED | THU | FRI |
|---|---|---|---|---|
| 1 | 2 | 3 | 4 | 5 ☆ JANUVIA SCHEDULED |
| 8 | 9 | 10 | 11 | 12 |
| 15 | 16 | 17 | 18 — 474 | 19 |
| 22 | 23 | 24 | 25 ☆ JANUVIA | 26 |
| 29 | 30 | 31 | 1 | 2 |

476 (pointing to Oct 5)

NOVEMBER

| MON | TUE | WED | THU | FRI |
|---|---|---|---|---|
| 29 | 30 | 31 | 1 | 2 ☆ VIT D-2 SCHEDULED |
| 5 | 6 | 7 | 8 | 9 |
| 12 | 13 | 14 | 15 | 16 |
| 19 | 20 | 21 ♡ ZOFRAN SCHEDULED / ☆ ATORVASTATIN SCHEDULED / ☆ BYDUREON SCHEDULED | 22 | 23 |
| 26 | 27 | 28 | 29 | 30 |

DYNAMIC USER INTERFACE GENERATION FOR DELIVERY SCHEDULING OPTIMIZATION

CROSS-REFERENCE TO RELATED APPLICATIONS

This application is a continuation of U.S. patent application Ser. No. 16/449,317 filed Jun. 21, 2019 (now U.S. Pat. No. 11,515,023), the entire disclosure of which is incorporated by reference.

FIELD

The present disclosure relates to computerized graphical user interfaces and, more particularly, to calendar-based graphical user interfaces.

BACKGROUND

Currently, entities such as high-volume pharmacies offer online drug management programs. For example, a user who is a member of a pharmacy can create an account using a user device to access the drug management program. Each user may be able to access their information and may be presented with a user interface illustrating their prescription history and/or insurance information. Users may be able to request drug refills and review delivery information.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A delivery scheduling method includes receiving a bundle request from a user and identifying a first prescription scheduled for delivery within a first date range. The method includes setting a scheduled delivery date of the first prescription as a target delivery date and identifying a set of prescriptions scheduled for delivery within a predetermined time of the target delivery date. The method includes selecting one of the set of prescriptions as a candidate prescription and obtaining prescription parameters of the candidate prescription including a prior fill date of the candidate prescription. The method includes determining a required fill date of the candidate prescription. The required fill date is a latest fill date of the candidate prescription to deliver the candidate prescription by the target delivery date. The method includes determining a blackout window for the candidate prescription based on a predetermined window following a prior fill date of the candidate prescription and, in response to the required fill date being after the blackout window, adjusting a delivery date of the candidate prescription to the target delivery date.

In other features, the first date range encompasses a predetermined period of time following a present date on which the bundle request is made. In other features, the method includes, in response to the required fill date being within the blackout window, updating the target delivery date by determining an earliest fill date of the candidate prescription following the blackout window and determining an earliest delivery date of the candidate prescription based on the earliest fill date of the candidate prescription.

Updating the target delivery date also includes setting the target delivery date to the earliest delivery date. The method includes repeating the selecting, obtaining, determining, adjusting, and updating steps. In other features, the method includes adding each prescription scheduled for delivery within the predetermined time of the target delivery date to a bundle list and, for each prescription in the bundle list, setting the prescription in the bundle list as the candidate prescription and performing the selecting, obtaining, determining, adjusting, and updating steps.

In other features, the method includes, in response to the delivery date of the candidate prescription being earlier than the target delivery date, determining a days supply on hand of the candidate prescription for the user as of the target delivery date and, in response to the days supply on hand being less than a first threshold, removing the candidate prescription from the bundle list. In other features, the method includes, in response to the days supply on hand being greater than the first threshold but less than a second threshold, generating an alert indicating the days supply on hand is below the second threshold and selectively transmitting the alert to the user. In other features, the method includes, in response to the candidate prescription being a refill prescription, performing the determining the blackout window. In other features, the method includes, in response to the candidate prescription being a new prescription not having been filled before, skipping determining the blackout window with respect to the candidate prescription.

In other features, the method includes, in response to a scheduling request for a new prescription, scheduling the new prescription for delivery by obtaining prescription parameters of the new prescription. In other features, scheduling the new prescription for delivery further includes, in response to a requested delivery date not being specified for the new prescription, determining an earliest fill date of the new prescription, determining an earliest delivery date of the new prescription based on the earliest fill date and delivery time, and setting a delivery date of the new prescription to the earliest delivery date.

In other features, scheduling the new prescription for delivery further includes, in response to the requested delivery date being specified for the new prescription, determining the earliest fill date of the new prescription and determining a requested fill date of the new prescription based on the requested delivery date of the new prescription. The method further includes, in response to the requested fill date being later than the earliest fill date, setting the delivery date of the new prescription to the requested delivery date. The method further includes, in response to the requested fill date being earlier than the earliest fill date, determining the earliest delivery date of the new prescription based on the earliest fill date and setting the delivery date of the new prescription to the earliest delivery date.

In other features, the prescription parameters include a prescribing physician, a drug identification, a drug dosage, a name of the user, and an address of the user. In other features, the prescription parameters of the candidate prescription include the prior fill date of the candidate prescription in response to the prescription parameters indicating the candidate prescription is a refill.

A delivery scheduling system includes at least one processor and a memory storing instructions for execution on the at least one processor. The instructions, upon execution, cause the at least one processor to receive a bundle request from a user, identify a first prescription scheduled for delivery within a first date range, and set a scheduled delivery date of the first prescription as a target delivery date. The instructions, upon execution, further cause the at least one processor to identify a set of prescriptions scheduled for delivery within a predetermined time of the target delivery date, select one of the set of prescriptions as a candidate prescription, and obtain prescription parameters of the candidate prescription including a prior fill date of the candidate prescription. The instructions, upon execution, further cause the at least one processor to determine a required fill date of the candidate prescription. The required fill date is a latest fill date of the candidate prescription to deliver the candidate prescription by the target delivery date. The instructions, upon execution, further cause the at least one processor to determine a blackout window for the candidate prescription based on a predetermined window following a prior fill date of the candidate prescription and, in response to the required fill date being after the blackout window, adjust a delivery date of the candidate prescription to the target delivery date In other features, the first date range encompasses a predetermined period of time following a present date on which the bundle request is made. In other features, the instructions, upon execution, cause the at least one processor to, in response to the required fill date being within the blackout window, update the target delivery date by determining an earliest fill date of the candidate prescription following the blackout window, determining an earliest delivery date of the candidate prescription based on the earliest fill date of the candidate prescription, and setting the target delivery date to the earliest delivery date. The method includes repeating the select, obtain, determine, adjust, and update steps.

In other features, the instructions, upon execution, cause the at least one processor to add each prescription scheduled for delivery within the predetermined time of the target delivery date to a bundle list and, for each prescription in the bundle list, set the prescription in the bundle list as the candidate prescription and perform the select, obtain, determine, adjust, and update steps. In other features, the instructions, upon execution, cause the at least one processor to, in response to the delivery date of the candidate prescription being earlier than the target delivery date, determine a days supply on hand of the candidate prescription for the user as of the target delivery date and, in response to the days supply on hand being less than a first threshold, remove the candidate prescription from the bundle list.

In other features, the instructions, upon execution, cause the at least one processor to, in response to the days supply on hand being greater than the first threshold but less than a second threshold, generate an alert indicating the days supply on hand is below the second threshold and selectively transmit the alert to the user.

In other features, the instructions, upon execution, cause the at least one processor to, in response to a scheduling request for a new prescription, schedule the new prescription for delivery by obtaining prescription parameters of the new prescription and, in response to a requested delivery date not being specified for the new prescription, determining an earliest fill date of the new prescription, determining an earliest delivery date of the new prescription based on the earliest fill date and delivery time, and setting a delivery date of the new prescription to the earliest delivery date.

In other features, scheduling the new prescription for delivery further includes, in response to the requested delivery date being specified for the new prescription, determining the earliest fill date of the new prescription and determining a requested fill date of the new prescription based on the requested delivery date of the new prescription. In other features, scheduling the new prescription for delivery further includes, in response to the requested fill date being later than the earliest fill date, setting the delivery date of the new prescription to the requested delivery date and, in response to the requested fill date being earlier than the earliest fill date, determining the earliest delivery date of the new prescription based on the earliest fill date and setting the delivery date of the new prescription to the earliest delivery date.

A non-transitory computer-readable medium stores processor-executable instructions. The instructions include receiving a bundle request from a user and identifying a first prescription scheduled for delivery within a first date range. The instructions further include setting a scheduled delivery date of the first prescription as a target delivery date and identifying a set of prescriptions scheduled for delivery within a predetermined time of the target delivery date. The instructions further include selecting one of the set of prescriptions as a candidate prescription and obtaining prescription parameters of the candidate prescription including a prior fill date of the candidate prescription. The instructions further include determining a required fill date of the candidate prescription. The required fill date is a latest fill date of the candidate prescription to deliver the candidate prescription by the target delivery date. The instructions further include determining a blackout window for the candidate prescription based on a predetermined window following a prior fill date of the candidate prescription and, in response to the required fill date being after the blackout window, adjusting a delivery date of the candidate prescription to the target delivery date.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIGS. 4A-4B together are an example prescription delivery scheduling interface depicting a calendar view of scheduled deliveries of prescription drugs.

FIGS. 5A-5B together are an example prescription delivery scheduling interface depicting a calendar view of a selected prescription drug scheduled for delivery.

FIGS. 6A-6B together are an example prescription delivery scheduling interface depicting a calendar view of scheduled deliveries of prescription drugs with bundled delivery dates.

FIGS. 7A-7B together are an example prescription delivery scheduling interface depicting a calendar view of scheduled deliveries including a prescription that is being processed resulting in a rescheduling of the delivery of the prescription not being guaranteed.

FIGS. 8A-8B together are an example prescription delivery scheduling interface depicting blocking out dates that are too soon to refill a prescription when a user is performing a drag operation.

FIGS. 9A-9B together are an example prescription delivery scheduling interface depicting a calendar view of scheduled deliveries confirming a rescheduled delivery.

In the drawings, reference numbers may be reused to identify similar and/or identical elements.

DETAILED DESCRIPTION

Figure 1:
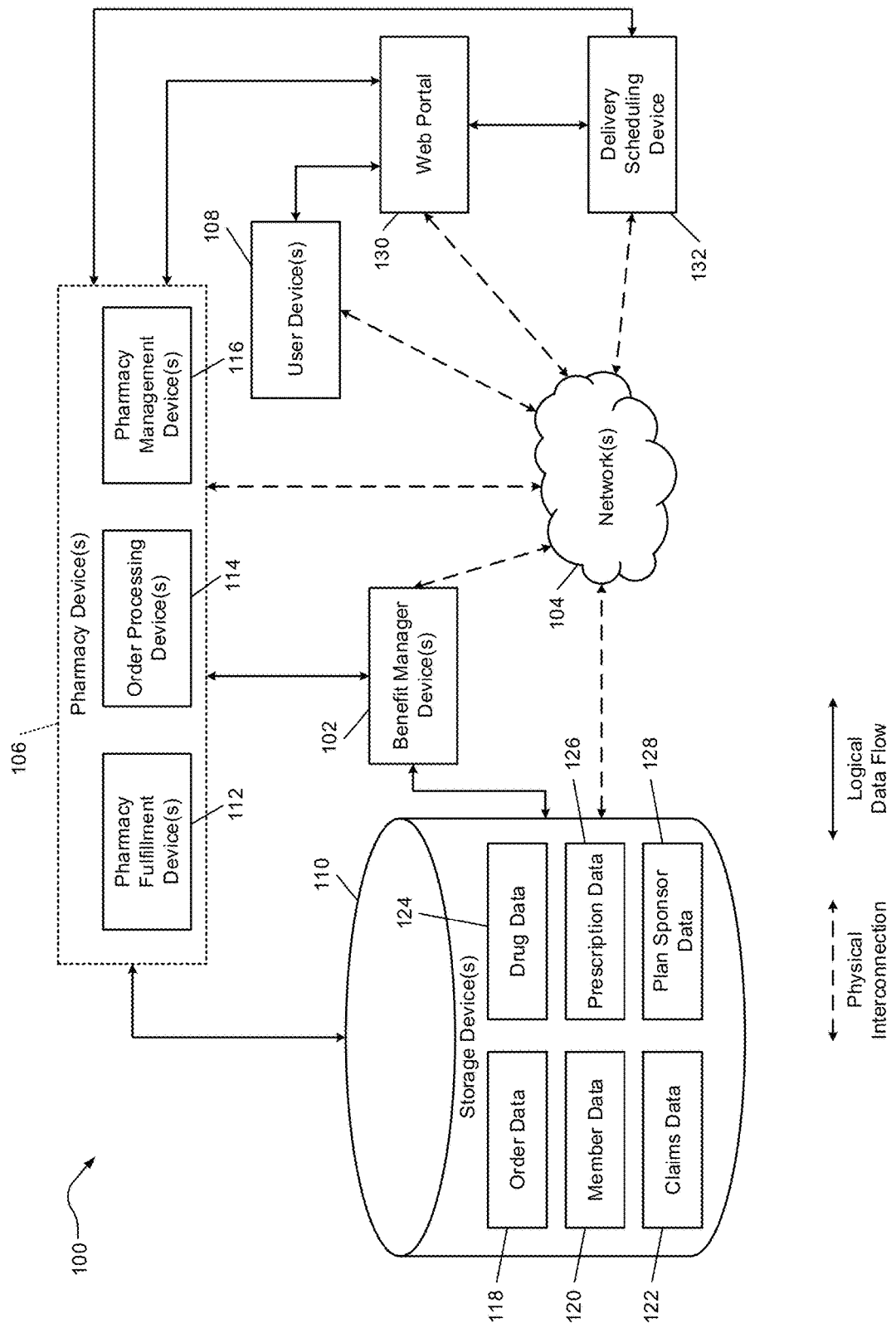
FIG. 1 is a functional block diagram of an example system including a high-volume pharmacy.

A prescription delivery scheduling device offers an interactive user interface where user-guided automation can adjust scheduled prescription delivery dates according to user preferences. The prescription delivery scheduling device controls a prescription delivery calendar, accessible using a web portal, that displays a calendar view of scheduled delivery dates of each of the user's prescriptions. In various implementations, the user creates login credentials through their pharmacy, pharmacy benefit manager (PBM), insurance provider, etc., to access a personalized user account.

Through the personalized user account, the user can access their prescription delivery calendar and adjust scheduled prescription delivery dates. The prescription delivery calendar may include prescriptions of all individuals listed on the insurance of the user. In various implementations, the user can designate which individuals are included on the user's prescription delivery calendar. The user may be able to delegate access to or control of their prescription delivery calendar. For example, the user may delegate access to their prescription delivery calendar to a caregiver on a separate insurance plan. Additionally, the user can designate access to their prescription delivery calendar to a facility, such as an assisted living facility, hospital, etc. In various implementations, the prescription delivery calendar may be filtered according to the prescription type, patient identity, date range, etc.

The user may adjust a delivery date of a scheduled prescription using a drag-and-drop operation. The prescription delivery scheduling device may receive a delivery date adjustment request, such as the initiation of a drag-and-drop operation by the user, and may determine whether the delivery date of the scheduled prescription can be updated to a requested delivery date.

The prescription delivery scheduling device considers the capacity of a pharmacy assigned to fill the scheduled prescription to determine an earliest possible fill date of the scheduled prescription. The earliest possible fill date of the scheduled prescription will determine the earliest possible delivery date of the prescription. Therefore, in instances of the user attempting to adjust the delivery date of the scheduled prescription to an earlier date, the prescription delivery scheduling device may calculate whether the assigned pharmacy is capable of fulfilling an order in time to make the requested delivery date.

In various implementations, for a refill prescription, the prescription delivery scheduling device also considers a measure of how much of the prior prescription remains with the user. For example, a measure called days supply on hand (DSOH) indicates how many days—assuming the user followed the previously-prescribed dosing regimen—of the prescription remain with the user on a certain date. The DSOH may be calculated for the order date of the refill prescription or for the delivery date of the refill prescription. If the user were to adjust the delivery date of the refill prescription to a later date, the prescription delivery scheduling device may warn the user if the DSOH of the previously filled prescription would fall below a threshold amount prior to the new delivery date. When the DSOH of a prescription falls below the threshold amount, there is a risk that any delay in the user obtaining the refill could result in a gap in care (missing one or more doses of the prescription).

In various implementations, the prescription delivery scheduling device also prevents the user from scheduling a refill prescription too early. For example, business rules may prevent certain drugs from being refilled too close to the most recent fill of the same prescription. For example, these business rules may be established according to federal, state, and local regulations, insurance plan requirements, PBM requirements, drug manufacturer guidelines, doctor directives, etc.

Therefore, if the user is adjusting the delivery date of a refill prescription, the prescription delivery scheduling device can calculate an earliest possible delivery date of the refill prescription based on a prior fill and a present date. The prescription delivery scheduling device may then instruct the prescription delivery calendar to visibly block out all dates prior to the earliest possible delivery date of the refill prescription. In various implementations, the prescription delivery scheduling device will prevent the user from dragging and dropping the refill prescription to a date prior to the earliest possible delivery date of the refill prescription.

The prescription delivery calendar provides the user with the ability to simply and efficiently adjust delivery dates of their prescriptions within the requirements and regulations of an operator of the prescription delivery scheduling device, such as the PBM, without having to parse fine print or research refill rules. The prescription delivery calendar further allows the user to log in to their account to determine when prescriptions will be delivered, giving the user more autonomy and reducing a number of calls to the PBM inquiring as to the delivery status of a prescription.

The prescription delivery calendar further provides an optimization technique to reduce the number of days on which the user receives prescription deliveries and to reduce the total number of deliveries received. This creates efficiencies for the user, especially in situations where the user may need to be home to accept deliveries and in situations where the location of deliveries is less convenient (for example, at a central office of an apartment complex).

The optimization technique bundles scheduled prescriptions within a predetermined time of one another to a single delivery date. For example, if, during the same week, a prescription is scheduled to be delivered on Monday, Wednesday, and Friday, the optimization technique may allow all of the scheduled prescriptions to be adjusted to a single delivery date, such as Monday. In fact, the scheduled prescriptions may even arrive in a single package. When bundling is requested, the prescription delivery scheduling device determines whether a selected scheduled prescription can be moved to a nearby delivery date based on (i) an ability to fill the prescription by an assigned pharmacy to meet the nearby delivery date, (ii) the DSOH of the selected scheduled prescription, and (iii) whether adjusting the delivery date would result in refilling the selected scheduled prescription too soon.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Fulfillment Device

Figure 2:
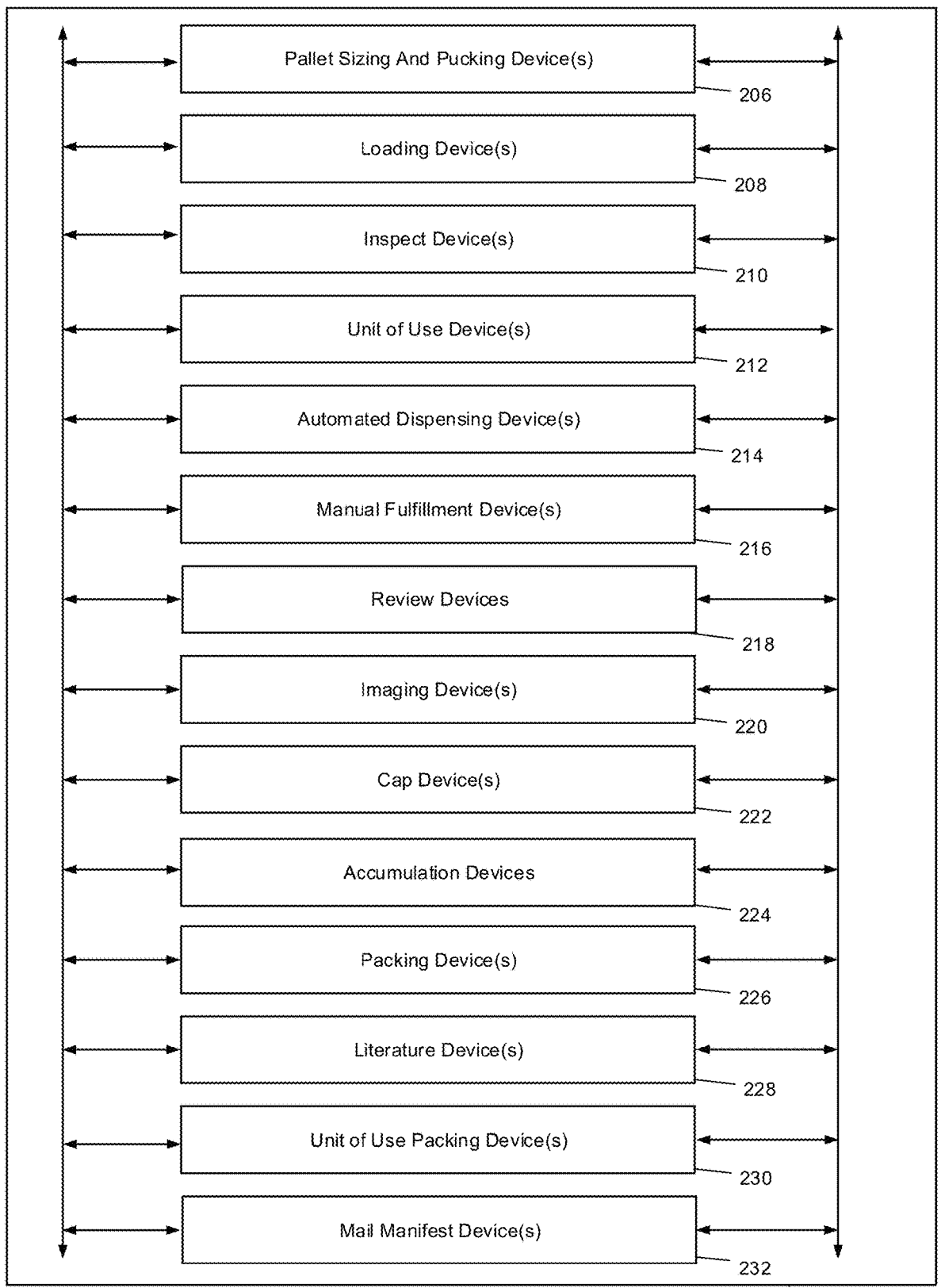
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
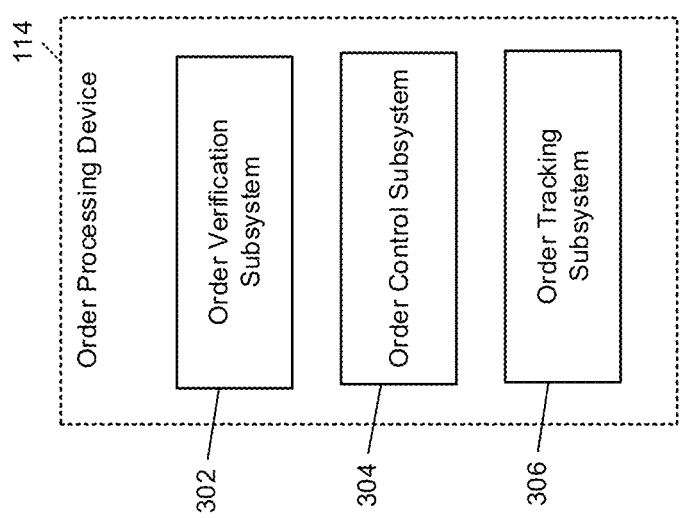
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Referring back to FIG. 1, a user device 108 may be used to access a web portal 130 to create an account with the user's pharmacy or PBM and access a prescription delivery calendar that includes scheduled prescription deliveries of the user. The user device 108 may be a desktop computer, kiosk, or mobile computing device, such as a phone or tablet.

Calendar Interface

Figure 4A:
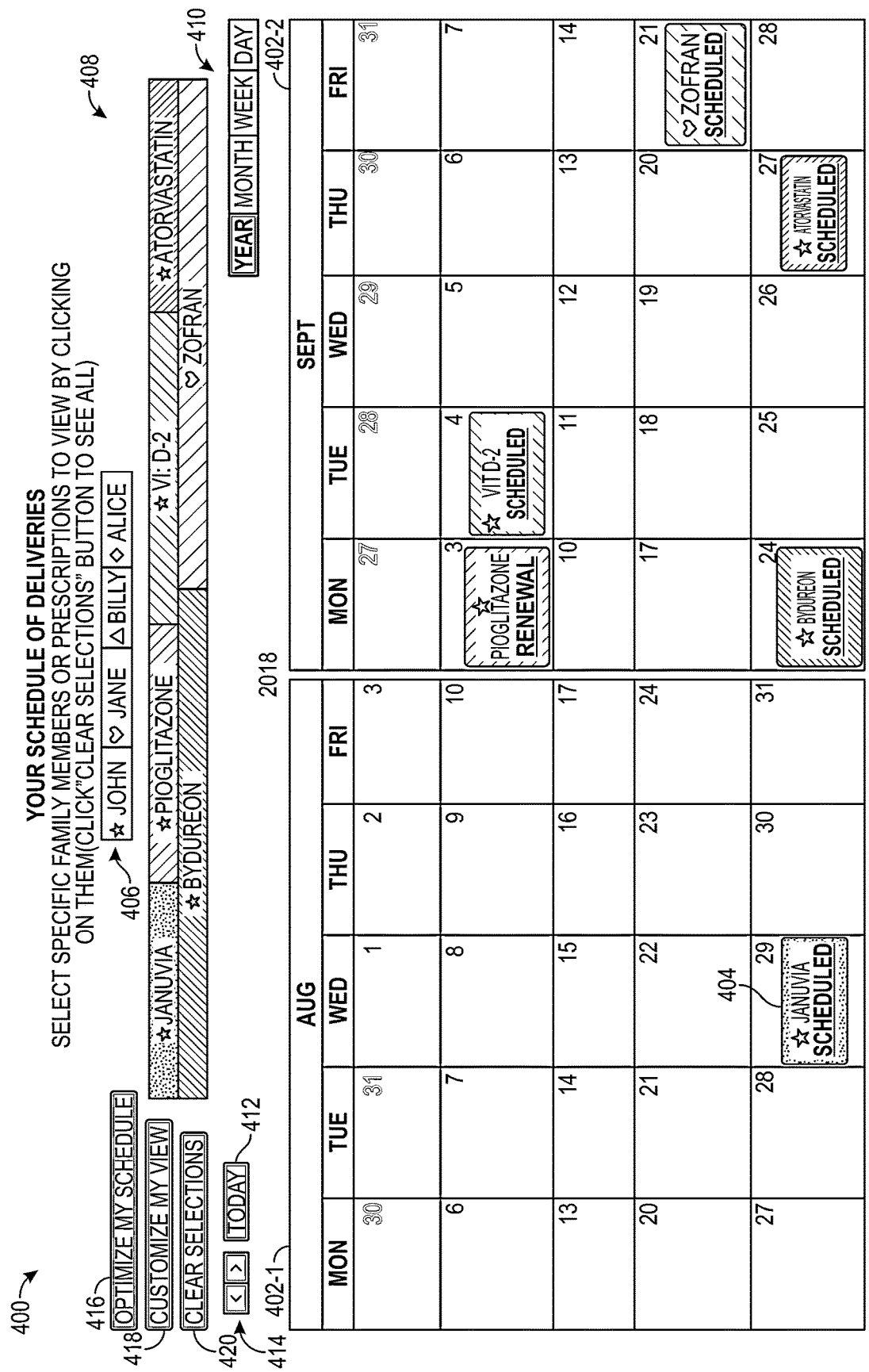

FIGS. 4A-4B are an example scheduling interface 400 depicting a calendar view of scheduled deliveries of prescription drugs for a particular user. For example, the user may have an account through their pharmacy or PBM. Upon authenticating to the scheduling interface 400 using their account, the scheduling interface 400 obtains the prescription information associated with the user's account.

The scheduling interface 400 may be interactive, allowing the user to adjust scheduled prescription deliveries for delivery on a different day using, for example, a drag-and-drop operation. The drag-and-drop operation may be performed by a cursor control device (such as a mouse) or directly on a display screen, such as with a finger or stylus. New prescriptions can be scheduled and displayed on the scheduling interface 400 once processed by the user's PBM. For example, during typical processing, once a new prescription is received, a prescription delivery scheduling device may receive the new prescription and, once the prescription is scheduled for delivery, the prescription delivery scheduling device may update the scheduling interface 400 to include the new prescription on the corresponding scheduled delivery date.

The scheduling interface 400 displays monthly calendars 402-1 and 402-2, shown in FIG. 4A, and monthly calendars 402-3 and 402-4, shown in FIG. 4B, with each scheduled prescription delivery listed on a scheduled delivery date of the scheduled prescription. As shown, a scheduled delivery 404 of Januvia brand tablets is scheduled for Aug. 29, 2018. In various implementations, each user's account may include prescriptions for a set of individuals, such as a family under the same prescription benefits program. FIG. 4A shows a set of individuals 406 named John, Jane, Billy, and Alice. To distinguish which prescription delivery corresponds to which individual, each individual may have a particular graphical signature, such as a color, shape, or symbol. In FIG. 4A, for example, John has a star displayed next to his name. Therefore, any scheduled delivery including a star, such as the scheduled delivery 404, corresponds to John.

The scheduling interface 400 may include a user interface (UI) element for each of the set of individuals that allows the displayed scheduled deliveries to be narrowed to a proper subset of the set of individuals (such as a single individual). For example, in FIG. 4A, four buttons are shown, corresponding to the four individuals. Selecting the button for John causes all scheduled deliveries for individuals other than John to be hidden. In other implementations, selecting the button for John may alternately show and hide the scheduled deliveries for John—in other words, each of the four buttons would act as a toggle.

A set of scheduled prescription deliveries 408 is displayed on the scheduling interface 400. UI elements may allow the user to filter what is being shown. For example, the scheduling interface 400 includes year, month, week, and day buttons 410, allowing the user to filter the view according to a time period. Additionally, a today button 412 allows the user to, upon selection, view the scheduled prescription deliveries for the present day. Forward and backward buttons 414 allow the user to view a previous or next screen of scheduled prescription deliveries (such as an adjacent pare of months).

The scheduling interface 400 includes a schedule optimization button 416 that, upon selection, optimizes the scheduling of prescription deliveries by attempting to reduce the number of days that prescriptions will be delivered, also referred to as bundling. A view customization button 418 allows the user to provide a custom date range as well as select which individuals and prescriptions the user desires to view. A clear selection button 420 resets the calendar view to a default view. For example, the default view may cover a predetermined time, such as four months, and cause scheduled deliveries for all individuals to be visible.

Figure 5A:
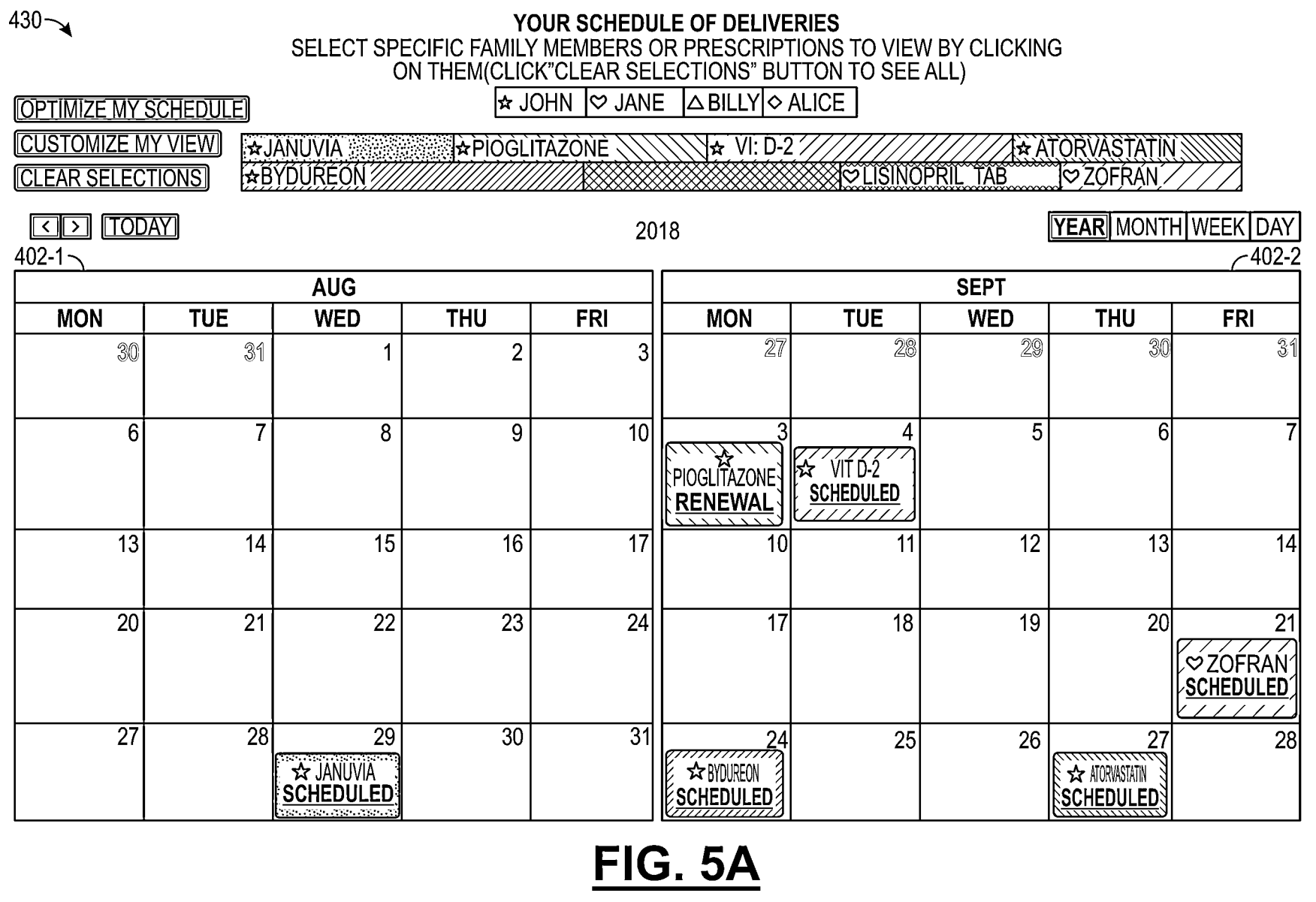
Figure 5B:
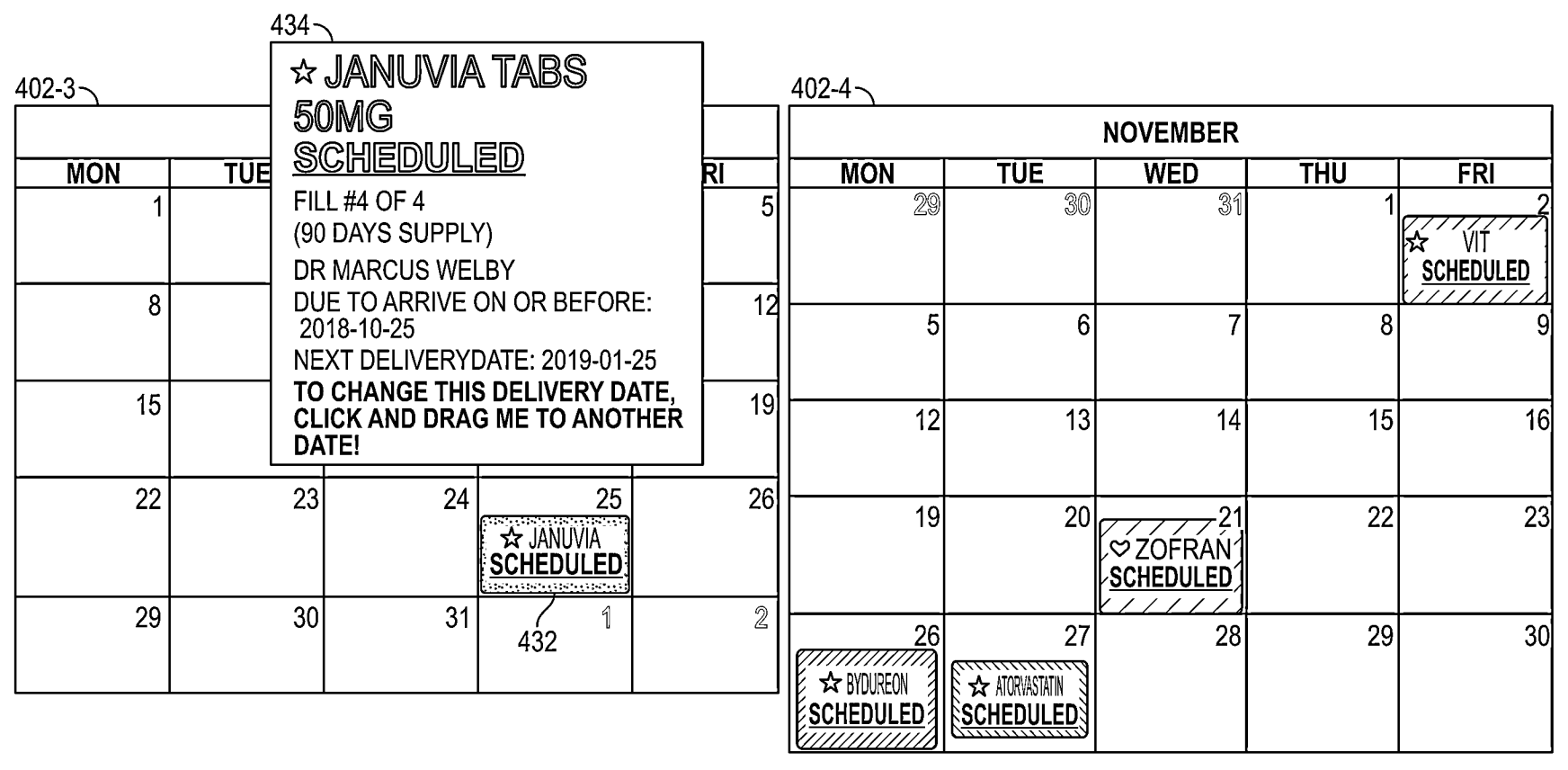

FIGS. 5A-5B are another view 430 of an example user interface. In FIG. 5B, a scheduled delivery 432 (in this case, Januvia brand tablets scheduled for Oct. 25, 2018) has been selected by a user. Upon user selection of the scheduled delivery 432, the interface displays additional information about the scheduled delivery 432 in an information box 434. For example, the information box 434 may include one or more of a fill number, an amount of medication included in the order, a prescribing physician, a delivery date, and a subsequent delivery date for a refill of the scheduled delivery 432.

Figure 6B:
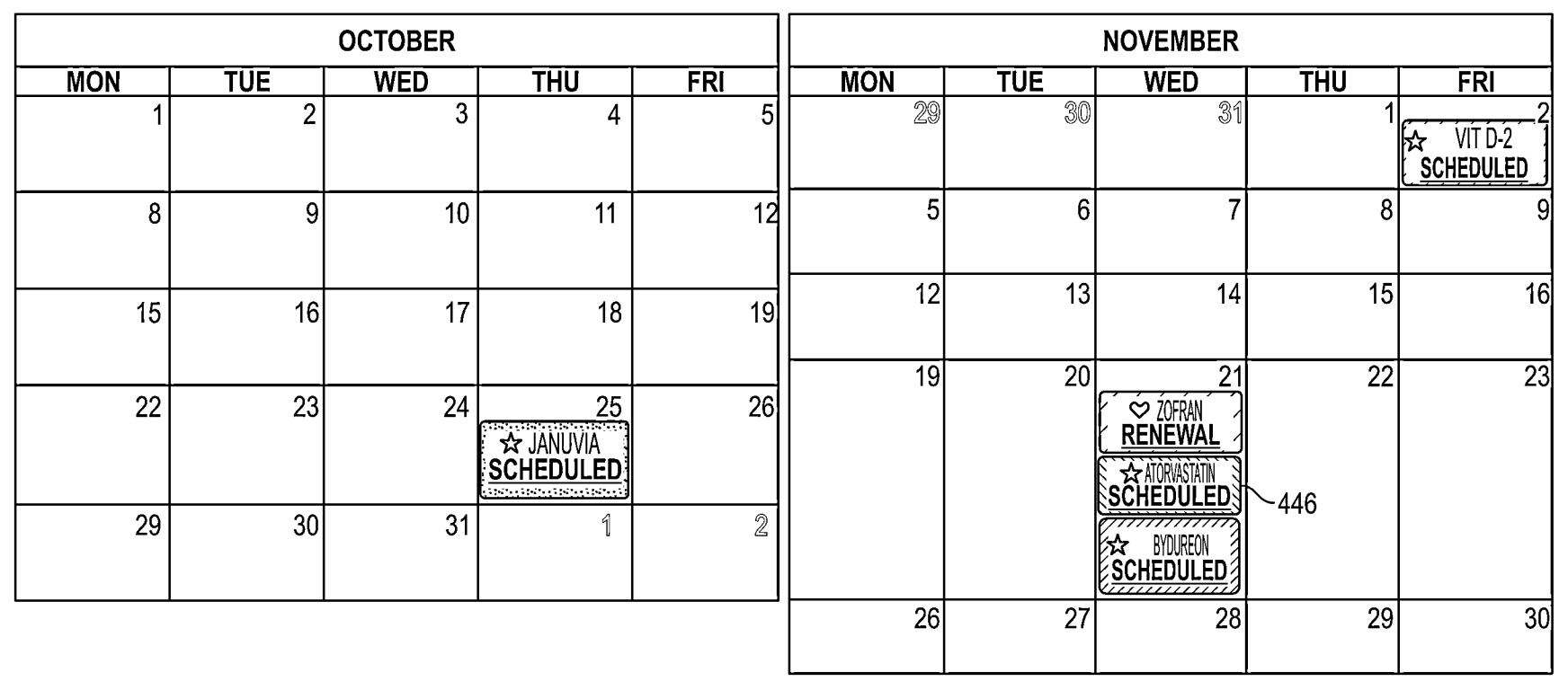

FIGS. 6A-6B are another view 440 of an example user interface following date bundling of scheduled deliveries. As described above and shown in FIG. 6A, the user may select the schedule optimization button 416 to adjust delivery dates of scheduled deliveries to reduce the number of delivery dates (and potentially, the number of delivered packages) for the user. In FIGS. 4A-5B, a delivery of Pioglitazone was scheduled for delivery on Sep. 3, 2018, a delivery of Vitamin D2 was scheduled for September 4, a delivery of Zofran brand medication was scheduled for September 21, a delivery of Bydureon brand medication was scheduled for September 24, and a delivery of Atorvastatin was scheduled for September 27.

After selection of the schedule optimization button 416, the scheduled prescription delivery system adjusts the delivery date of Vitamin D2 earlier, into a first bundle 442 with Pioglitazone on September 3, reducing two days of deliveries to one. Similarly, the Bydureon delivery and the Atorvastatin delivery are adjusted earlier to a second bundle 444 to be delivered with Zofran on September 21. Similarly, a third bundle 446, including the same prescriptions as the second bundle 444, is created in November, reducing the total number of delivery dates in August through September from eleven to six.

The optimization mechanism is described in more detail below. In brief, one approach is for the scheduled prescription delivery system to first attempt to move prescriptions scheduled within a predetermined window of an earlier prescription to the earlier delivery date. For example, the Atorvastatin delivery day is moved to September 21 instead of the Zofran delivery date being moved to September 27. In various implementations, the delivery dates may be adjusted to a later date based on an inability (such as due to pharmacy capacity or prescription rules) to move a date earlier.

Figure 7B:
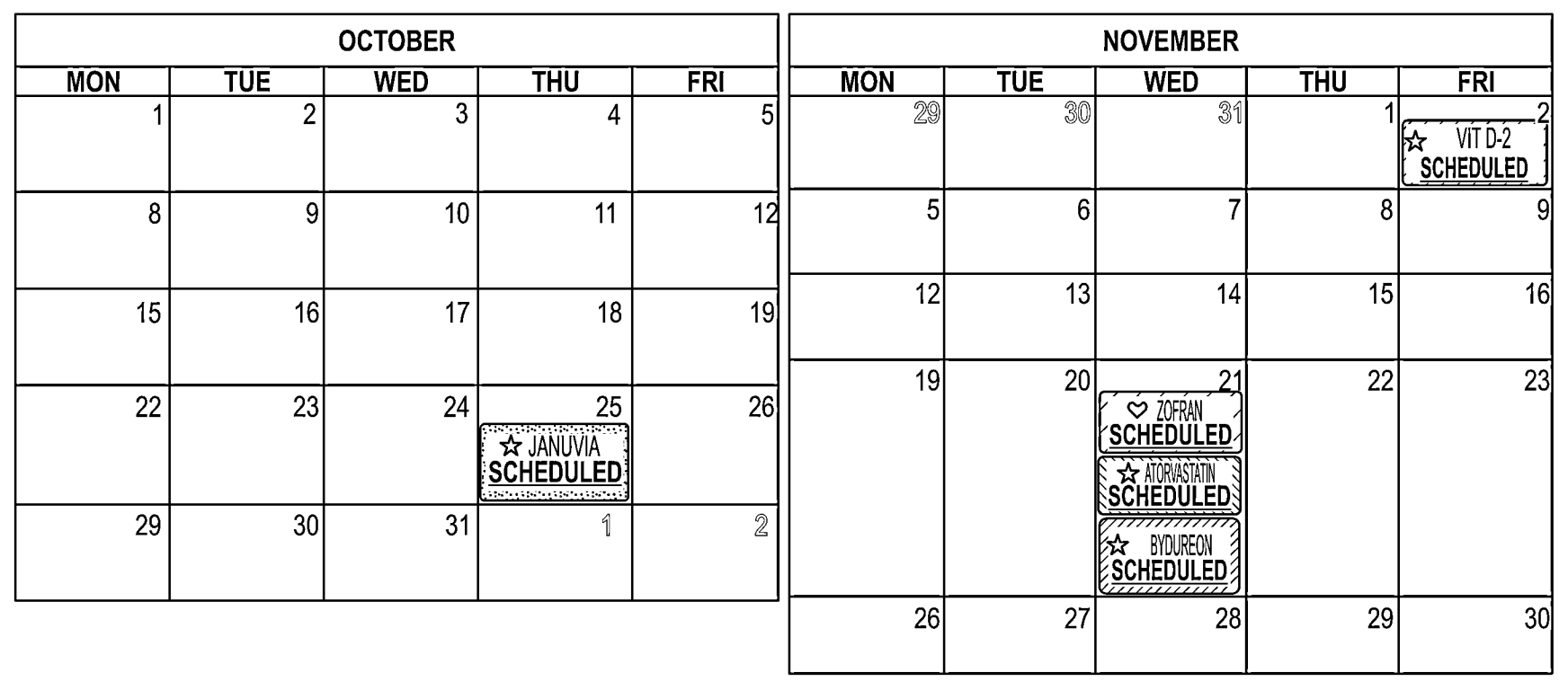

FIGS. 7A-7B are an example interface showing a delivery rescheduled close to the present date. In this example, FIG. 7A shows that a scheduled delivery 452 of Januvia brand tablets has been adjusted earlier in time. However, when the earlier date is close to the present date, the system may not be able to guarantee this new delivery date. The system may therefore display some sort of warning or guidance, such as a highlighted time frame 454 indicating a timeframe within which a scheduled delivery date is not guaranteed.

In various implementations, during a timeframe where rescheduling of a prescription delivery date is not guaranteed, the system may accept the rescheduling request but will not guarantee a particular delivery date. For example, the system may reschedule the delivery date but may not indicate the rescheduled delivery date as a guaranteed date on the example interface or otherwise. Instead, the system may maintain the original guaranteed delivery date as the guaranteed delivery date.

In FIG. 7A, the highlighted time frame 454 is the last week in August. In various implementations, the interface may prevent rescheduling during the highlighted time frame 454 or may display an alert in response to the delivery date of the scheduled delivery 452 being adjusted to within the highlighted time frame 454. The highlighted time frame 454 may be specific to each prescription—for example, based on the inventory, packaging time, and shipping time for the pharmacy expected to fulfill the prescription.

Figure 8A:
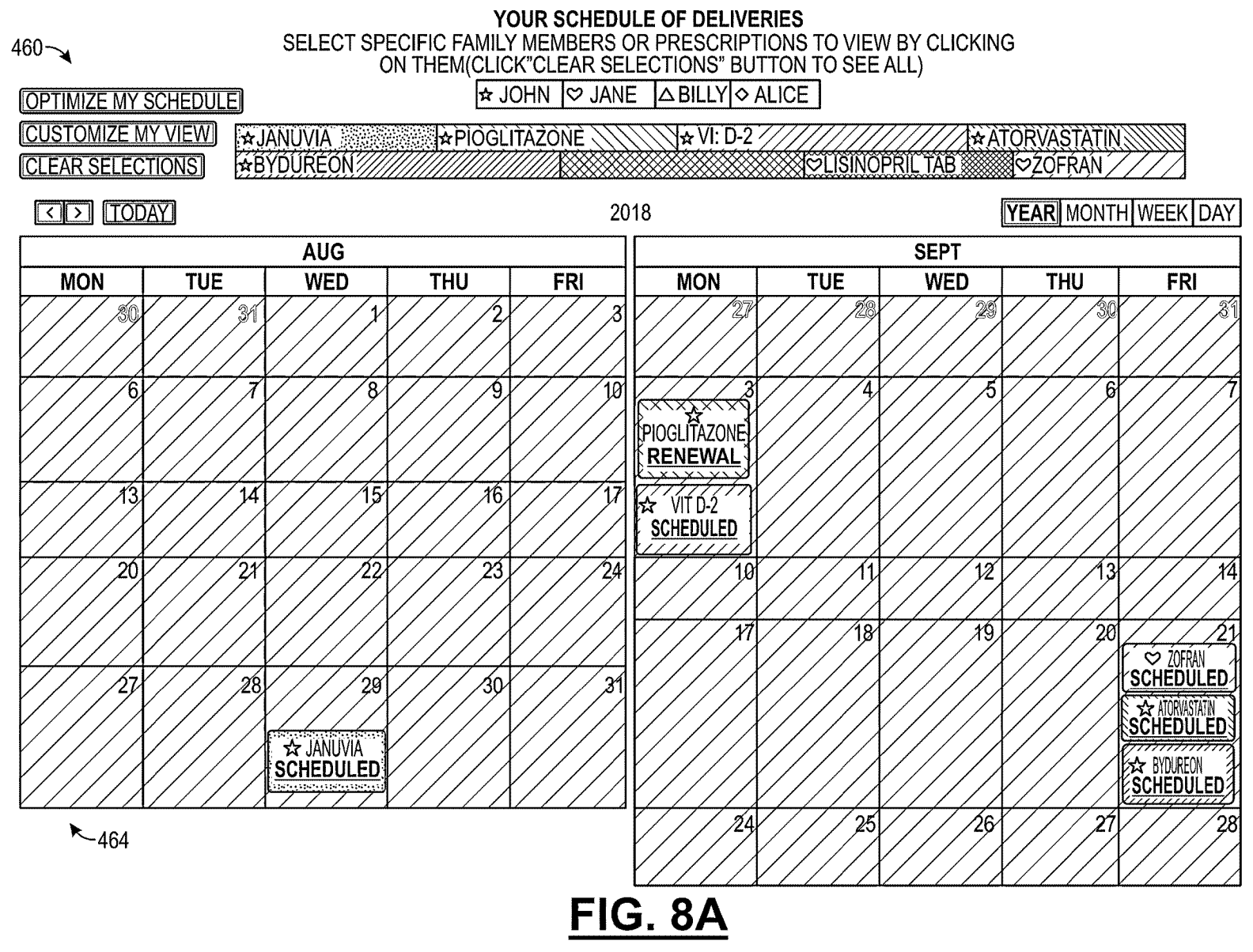

FIGS. 8A-8B are an example interface 460 depicting visually indicating dates that are too soon to refill a prescription, such as when a user is performing a drag-and-drop adjustment of a scheduled delivery. In various implementations, initiating a drag operation of a selected prescription 462 (shown in FIG. 8B) by a user may result in the prescription delivery scheduling screen of the interface 460 determining and then visually indicating the earliest possible refill date. The interface 460 may prevent the scheduled delivery from being placed prior to the earliest possible refill date. In various implementations, if the user drops the scheduled delivery into a timeframe prior to the earliest possible refill date, the interface 460 may then move the scheduled delivery to the earliest possible refill date.

For example, while the user is dragging the scheduled delivery, a visual indication may be applied to all dates prior to the earliest possible refill date. This visual indication may include, as examples, one or more of removing color (changing to grayscale), increasing transparency of the date text, applying a black or grey fill, or applying a hatched pattern.

As shown in FIG. 8A, the blocked-out dates 464 include all of August and September. For example, the selected prescription 462 may be a refill prescription and, according to insurance and regulatory guidelines, certain prescriptions may not be refilled within a predetermined amount of time of the previously filled prescription of the same type. Therefore, the earliest possible refill date may be calculated based on such refill requirements to be October 1. Therefore, when the user is attempting to move the selected prescription 462 from an original delivery date of October 25 to a new delivery date (such as October 5), dates prior to October 1 are blocked out as indicated at 464.

FIGS. 9A-9B are an example interface 470 depicting a scheduled delivery confirmation. In various implementations, when the user reschedules a scheduled delivery, a confirmation dialog 472 may prompt the user to confirm the rescheduling of the delivery date. This reduces the risk of inadvertent rescheduling while viewing upcoming prescription deliveries. In FIG. 9B, the user has dragged-and-dropped a scheduled delivery (in this case, Januvia brand medication) from the previously scheduled delivery date (October 25, indicated at 474) to a new delivery date (October 5, indicated at 476). In response to the user confirming the change in the confirmation dialog 472 displayed in FIG. 9A, the scheduled delivery is updated to October 5. If the user cancels the change, the scheduled delivery will remain scheduled for the original date of October 25.

In various implementations, the example interface may prompt the user with a worry-free refill confirmation request. If the user opts to enroll in worry free refills, the system automatically confirms prescription delivery dates for a number of refills included on the prescription. For example, if the prescription includes five refills, the system will automatically schedule prescription delivery dates for each of the five refills. Additionally, if the user grants renewal request permissions to the system (also received via a prompt on the example interface), the system will automatically prompt an administrator to request a prescription renewal for the prescription when the user's prescription and refills are nearing an end. That is, the administrator may contact the user's physician to request another prescription to facilitate prescription renewal for the user when the user's prescription is ending. In various implementations, the administrator may initiate prescription renewal early—for example, before a last prescription refill—to ensure the user's supply of the prescription does not lapse.

Prescription Delivery Scheduling Device

Figure 10:
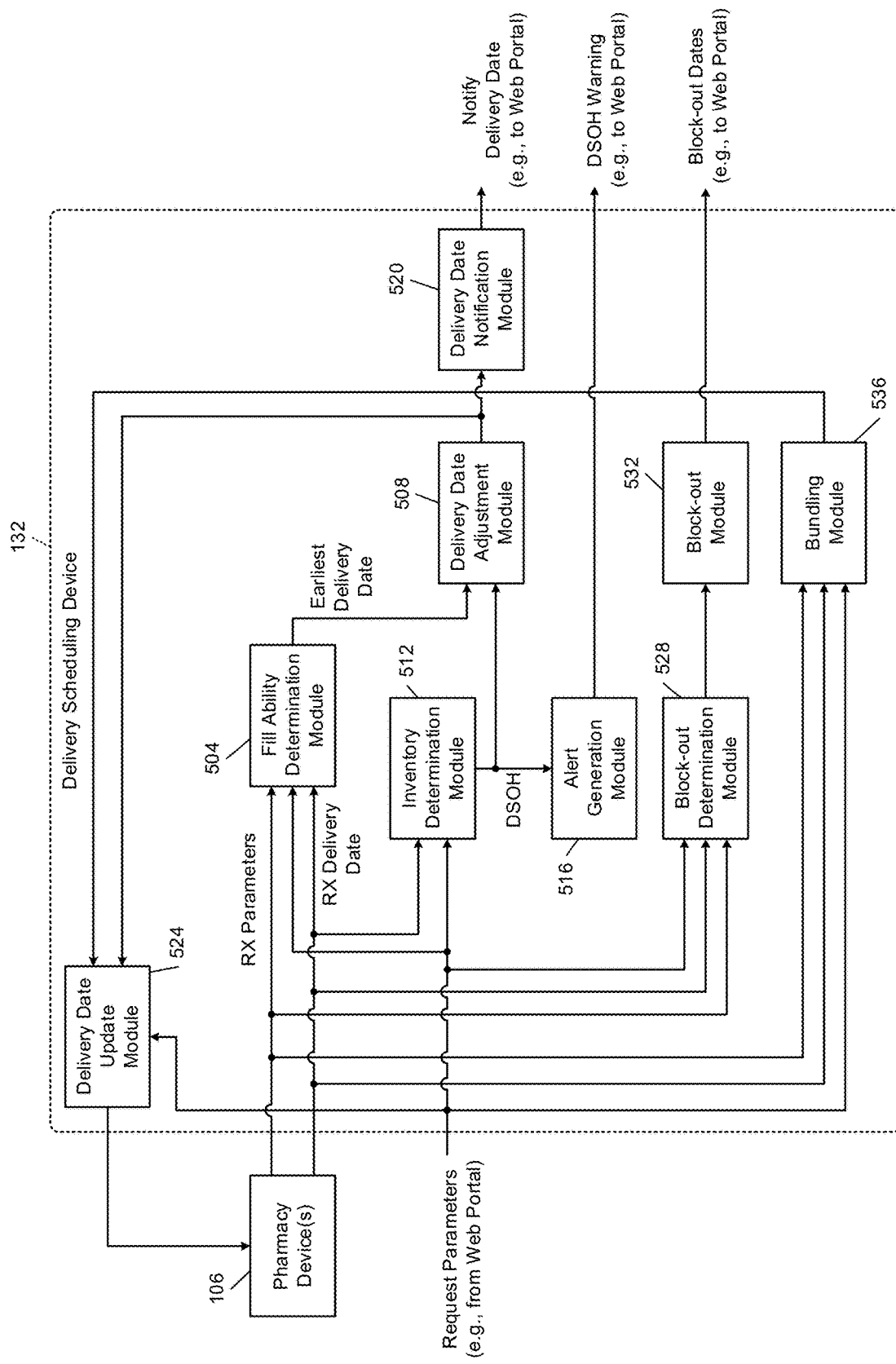
FIG. 10 is a functional block diagram of an example implementation of a prescription delivery scheduling device.

FIG. 10 is a functional block diagram of an example implementation of a delivery scheduling device 132. In various implementations, the interfaces described in FIGS. 4A-9B may be generated by the delivery scheduling device 132. The delivery scheduling device 132 may receive requests from the web portal 130 (shown in FIG. 1). For example, when a prescription is received by the PBM, a default delivery date is scheduled for the prescription. When the user accesses the web portal, they will see the default delivery date for the prescription.

In various implementations, the default delivery date may be assigned by the delivery scheduling device 132 in response to a scheduling request from the pharmacy device 106. In response to receiving the scheduling request, the delivery scheduling device 132 obtains prescription parameters of the prescription from the pharmacy device 106. The prescription parameters may include drug information, such as drug identification, dosage information, etc.; user identification information, such as name, address, etc.; refill information, such as delivery date of previously filled prescriptions of the same drug, etc.

Regardless of whether the delivery scheduling device 132 assigns a default delivery date, the web portal may provide a delivery date adjustment in response to user input, such as a drag-and-drop operation. For example, when the user is attempting to reschedule the delivery date of a scheduled prescription, the web portal will transmit a request along with request parameters to the delivery scheduling device 132. The request may also be generated in response to a bundling request, as by selection of the schedule optimization button 416 (shown in FIGS. 4A-9B).

Once the delivery scheduling device 132 receives a request, the delivery scheduling device 132 obtains the request parameters as well as the currently scheduled prescription delivery date (which may be stored by the pharmacy device 106). A fill ability determination module 504 receives the request parameters, the prescription parameters, and the scheduled prescription delivery date. The request parameters may indicate a type of request, such as an adjusted delivery date request when the user is performing the drag-and-drop operation, a bundling request when the user selects the schedule optimization button, etc.

In response to receiving a new prescription, uploaded to the web portal or obtained from the pharmacy device 106, the fill ability determination module 504 obtains prescription parameters of the new prescription (such as from the pharmacy device 106). Based on the prescription parameters, the fill ability determination module 504 calculates an earliest possible fill date of the new prescription based on pharmacy capacity. From the earliest possible fill date, the fill ability determination module 504 calculates an earliest possible delivery date, which is transmitted to a delivery date adjustment module 508.

As described below, the delivery date adjustment module 508 selects a delivery date that is the same as or later than the earliest possible delivery date, and transmits the earliest possible delivery date to update the pharmacy and the web portal. In various implementations, the fill ability determination module 504 may default to select the earliest possible delivery date. Alternatively, the fill ability determination module 504 may attempt to set a delivery date that is a predetermined amount of time from the original request (for example, two weeks). Then, the fill ability determination module 504 may attempt to determine whether the default delivery date can be met.

In response to receiving the requested delivery date or an adjusted delivery request, the fill ability determination module 504 determines whether the prescription can be delivered on the requested delivery date. For example, the fill ability determination module 504 determines a required fill date based on the requested delivery date. If the prescription can be filled by the required fill date, then the fill ability determination module 504 transmits the requested delivery date to a delivery date adjustment module 508. Alternatively, if the fill ability determination module 504 determines that the required fill date cannot be met, then the fill ability determination module 504 calculates an earliest fill date. A fill ability is determined based on prescription processing times as well as drug stock and order capacity at an assigned fulfillment pharmacy. Based on the earliest fill date, the fill ability determination module 504 calculates an earliest delivery date and forwards the earliest delivery date along with the requested delivery date to the delivery date adjustment module 508.

An inventory determination module 512 receives the request parameters, the prescription parameters, and the scheduled delivery date. In response to receiving the adjusted delivery date request and, based on the prescription parameters, the inventory determination module 512 determines whether the prescription is a refill prescription. If the prescription is a refill prescription, the inventory determination module 512 calculates a day supply on hand (DSOH) of the prescription. The inventory determination module 512 determines when the user received the most recent refill of the prescription and calculates, assuming 100% adherence, an amount of drug doses remaining in the user's possession (or, equivalently, DSOH). In various implementations, the inventory determination module 512 determines the DSOH only based on the most recent refill prescription receipt date and a stated duration of the prescription. In various implementations, the inventory determination module 512 may consider all past refill prescriptions to calculate the DSOH, assuming 100% adherence.

The inventory determination module 512 transmits the DSOH to the delivery date adjustment module 508 and an alert generation module 516. In response to the DSOH being less than or equal to a threshold amount, the alert generation module 516 transmits a DSOH warning to the web portal. For example, if delivering the prescription on the requested delivery date results in the user having, by the delivery day, a number of doses less than or equal to the threshold amount, the DSOH warning is transmitted to the web portal to warn the user.

The delivery date adjustment module 508 receives the requested delivery date and an approved delivery date from the fill ability determination module 504 as well as the DSOH from the inventory determination module 512. The delivery date adjustment module 508 determines whether the requested delivery date needs to be adjusted based on whether the approved delivery date deviates from the requested delivery date. If the approved delivery date deviates from the requested delivery date, the delivery date adjustment module 508 transmits a notification request to a delivery date notification module 520 along with the approved delivery date.

The delivery date notification module 520 generates a notification including the approved delivery date and transmits the notification including the approved delivery date to the web portal for display to the user. The delivery date adjustment module 508 also transmits the approved delivery date to a delivery date update module 524. The delivery date update module 524 also receives the request parameters and determines whether the delivery date was adjusted. In response to determining that the delivery date was adjusted, the delivery date update module 524 transmits the updated delivery date to the pharmacy device 106. When the approved delivery date does not deviate from the requested delivery date, the delivery date adjustment module 508 does not transmit the notification request to the delivery date notification module 520 and the delivery date update module 524 does not update the pharmacy device 106.

A block-out determination module 528 receives request parameters, prescription parameters, and the scheduled delivery date. If the request parameters include an indication the user is performing a drag-and-drop operation for the prescription using the web portal, the block-out determination module 528 identifies if the prescription is a refill based on the prescription parameters. If the prescription is not a refill, the block-out determination module 528 sends a present date to a block-out module 532. In various implementations, the block-out determination module 528 may, in response to the prescription not being a refill, calculate an earliest possible fill date of the prescription according to pharmacy capacity, the present date, etc. Based on the earliest possible fill date of the prescription, the block-out determination module 528 may calculate an earliest possible delivery date of the prescription. In this case, the block-out determination module 528 transmits the later of the earliest possible delivery date of the prescription and the present date to the block-out module 532.

If the block-out determination module 528 determines that the prescription is a refill, then the block-out determination module 528 determines the earliest possible fill date of the prescription based on a most recent fill date of a most recent refill. As described above, a number of prescriptions may only be refilled a predetermined delay after the user has received the most recent refill. For example, prescriptions may not be refilled too early based on insurance requirements as well as drug regulations. In various implementations, once the earliest possible fill date of the prescription is determined based on a most recent refill delivery date of the same drug, the block-out determination module 528 calculates an earliest possible delivery date based on the earliest possible fill date. The earliest possible delivery date is then forwarded to the block-out module 532.

Additionally or alternatively, the block-out determination module 528, as mentioned above, may calculate the earliest possible fill date based on capacity, such as pharmacy capacity, as described above, when the prescription is not a refill prescription. From the earliest possible fill date based on capacity, the earliest possible delivery date is determined. The block-out determination module 528 may then transmit the later of the following dates: the earliest possible delivery date based on the most recent refill delivery date, the earliest possible delivery date based on capacity, and the present date.

Based on the earliest possible delivery day, the block-out module 532 allows the web portal to visibly block out each date prior to the earliest possible delivery date. These dates are blocked out to visibly depict to the user that these dates are unavailable. In various implementations, the web portal does not allow the selected prescription to be moved to one of the blocked out dates established by the block-out module 532.

A bundling module 536 receives request parameters and, in response to the request parameters including a bundling request (such as, when the schedule optimization button is selected), the bundling module 536 obtains prescription parameters and scheduled prescription delivery dates according to a specified date range included in the request parameters. Then, the bundling module 536 adjusts the delivery dates of scheduled prescriptions within the specified date range to minimize the number of delivery dates. For example, one bundling approach is described in FIGS. 13A-13B.

In various implementations, the bundling module 536 will identify, for example, one week within the specified date range and determine if a scheduled prescription delivered later in the week can be adjusted to a scheduled prescription delivered earlier in the week. The bundling module 536 considers DSOH as well as factors similar to those described above with respect to an earliest possible fill date of prescriptions. If any scheduled prescriptions are bundled, the bundling module 536 transmits the new delivery dates associated with bundled prescriptions to the delivery date update module 524. The delivery date update module 524 updates any necessary delivery dates by sending adjusted delivery dates to the pharmacy device 106.

Flowcharts

Figure 11:
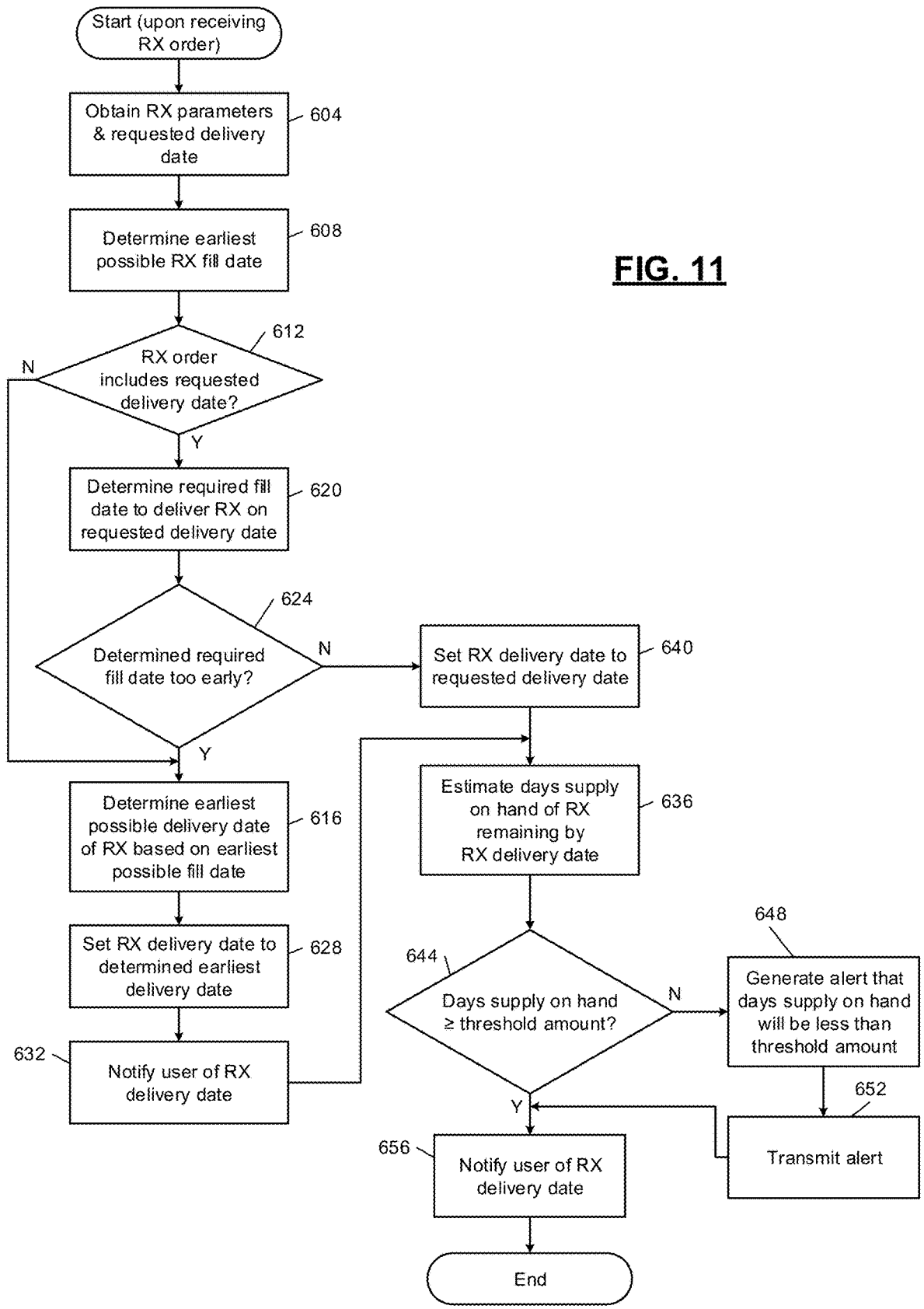
FIG. 11 is a flowchart of example operation of a prescription delivery date scheduling interface.

FIG. 11 is a flowchart of example prescription delivery date scheduling. Control begins upon receiving a prescription order. At 604, control obtains prescription parameters and a requested delivery date. Control continues to 608, where control determines an earliest possible prescription fill date. Control continues to 612 to determine whether the prescription order includes a requested delivery date. If not, control proceeds to 616 to determine an earliest possible delivery date of the prescription based on the earliest possible fill date; otherwise, control continues to 620, where control determines a required fill date to deliver the prescription on the requested delivery date.

At 624, control compares the required fill date and the earliest possible prescription filled date. If control determines that the required fill date is too early, control continues to 616 to determine the earliest possible delivery date of the prescription based on the earliest possible fill date. At 628, control sets a prescription delivery date to the determined earliest possible delivery date. Control continues to 632 to notify the user of the prescription delivery date. Control then proceeds to 636 to estimate the DSOH of the prescription as of the prescription delivery date.

If, at 624, the determined required fill date is not too early, control continues to 640, sets the prescription delivery date to the requested delivery date, and proceeds to 636. As described above, the DSOH is relevant when the prescription is a refill. The DSOH indicates the number of days of doses remaining with the user from the most recently filled prescription.

Control continues from 636 to 644 to determine whether the DSOH is greater than or equal to a threshold amount. If no, control proceeds to 648, where control generates an alert that the DSOH will be less than the threshold amount. Control then continues to 652, transmits the alert, and continues to 656. However, if at 644, the DSOH is greater than or equal to the threshold amount, control continues to 656. At 656, control notifies the user of the prescription delivery date and then ends. Notification of the user may take the form of a message in the web portal or a visual indication of a delivery date.

Figure 12:
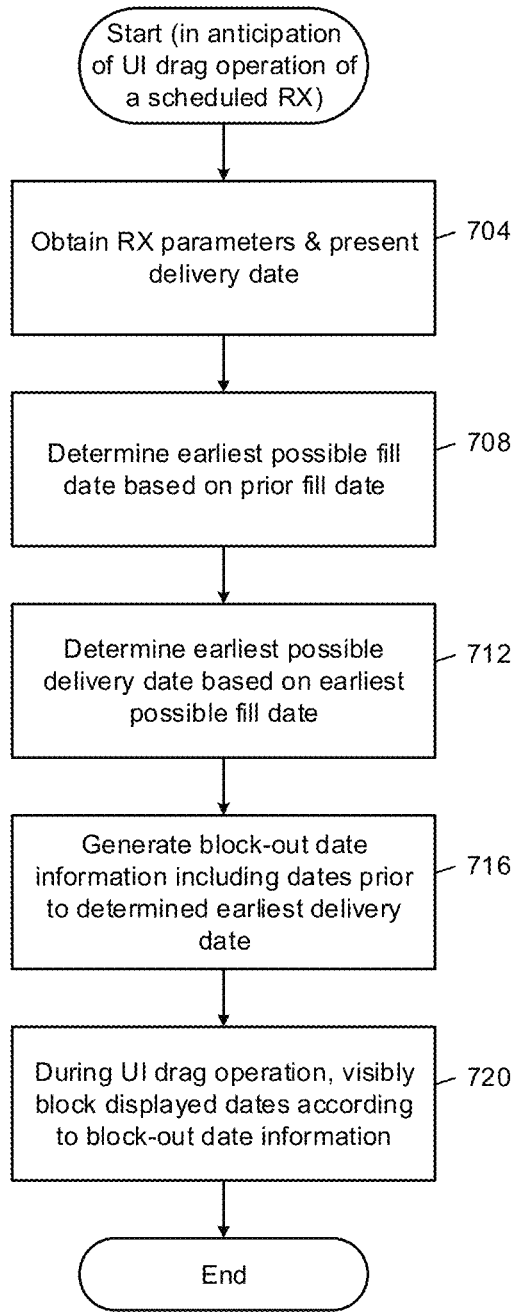
FIG. 12 is a flowchart of example delivery date block-out.

FIG. 12 is a flowchart of example delivery date block-out. Control begins at 704 upon a user selecting a scheduled delivery, which may indicate the beginning of, or the potential for, a drag-and-drop operation. At 704, control obtains prescription parameters and a present delivery date. Control continues to 708, where control determines an earliest possible fill date based on a prior fill date. At 712, control determines an earliest possible delivery date based on the earliest possible fill date. Control continues to 716 to generate block-out date information, including dates prior to the determined earliest possible delivery date. As described above, control calculates the earliest possible delivery date of the prescription based on a prior fill date, pharmacy capacity, and a present date.

At 720, during the user interface drag operation, control visibly blocks displayed dates according to the block-out date information. For example, the user interface grays out or prevents selection of dates prior to the earliest possible delivery date while the scheduled prescription is being dragged. In addition, control may prevent the delivery date of the scheduled prescription from being adjusted to a date prior to the earliest possible delivery date.

Figure 13A:
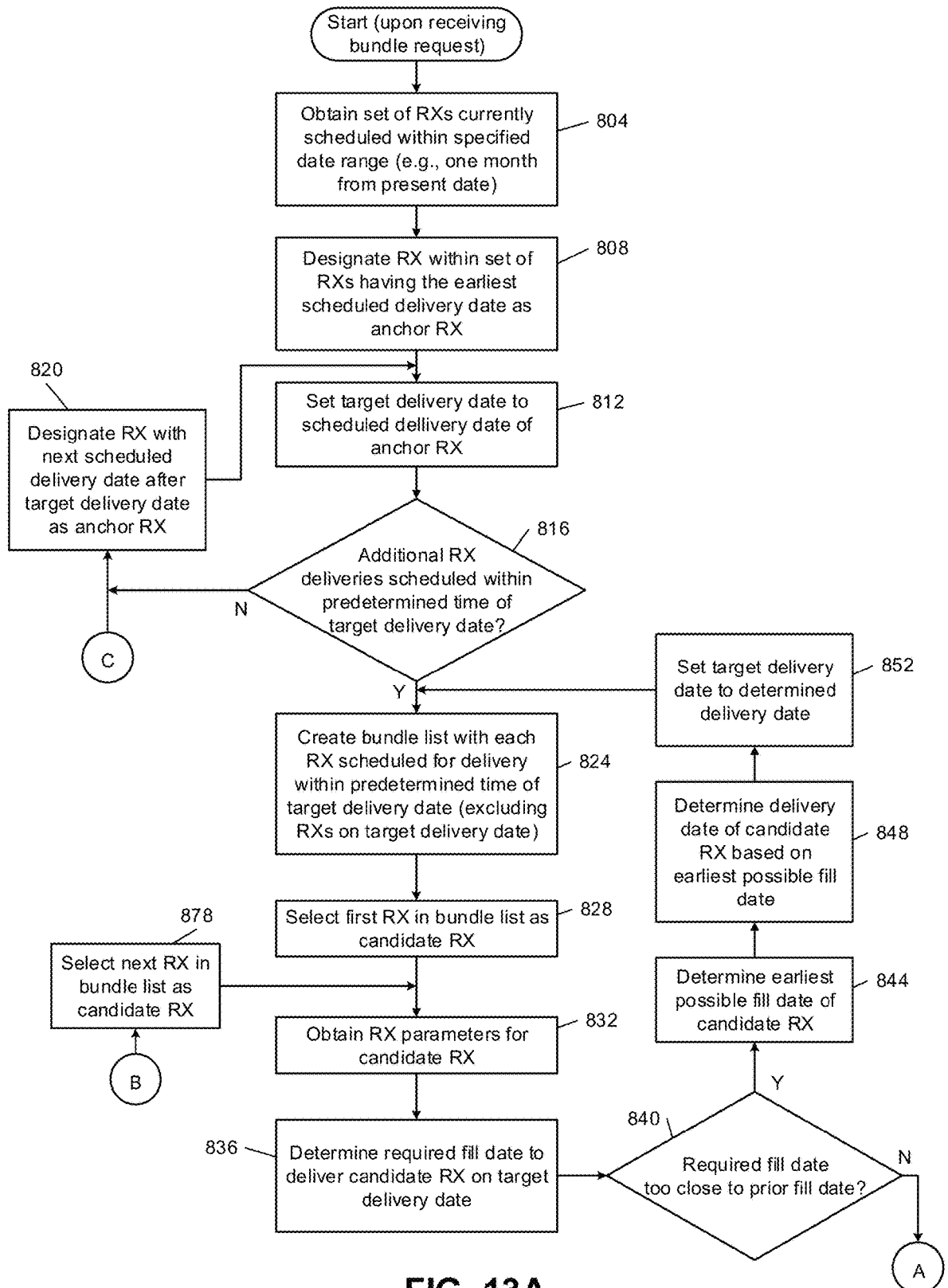
FIGS. 13A-13B together are a flowchart of example operation of automated prescription delivery date bundling.
Figure 13B:
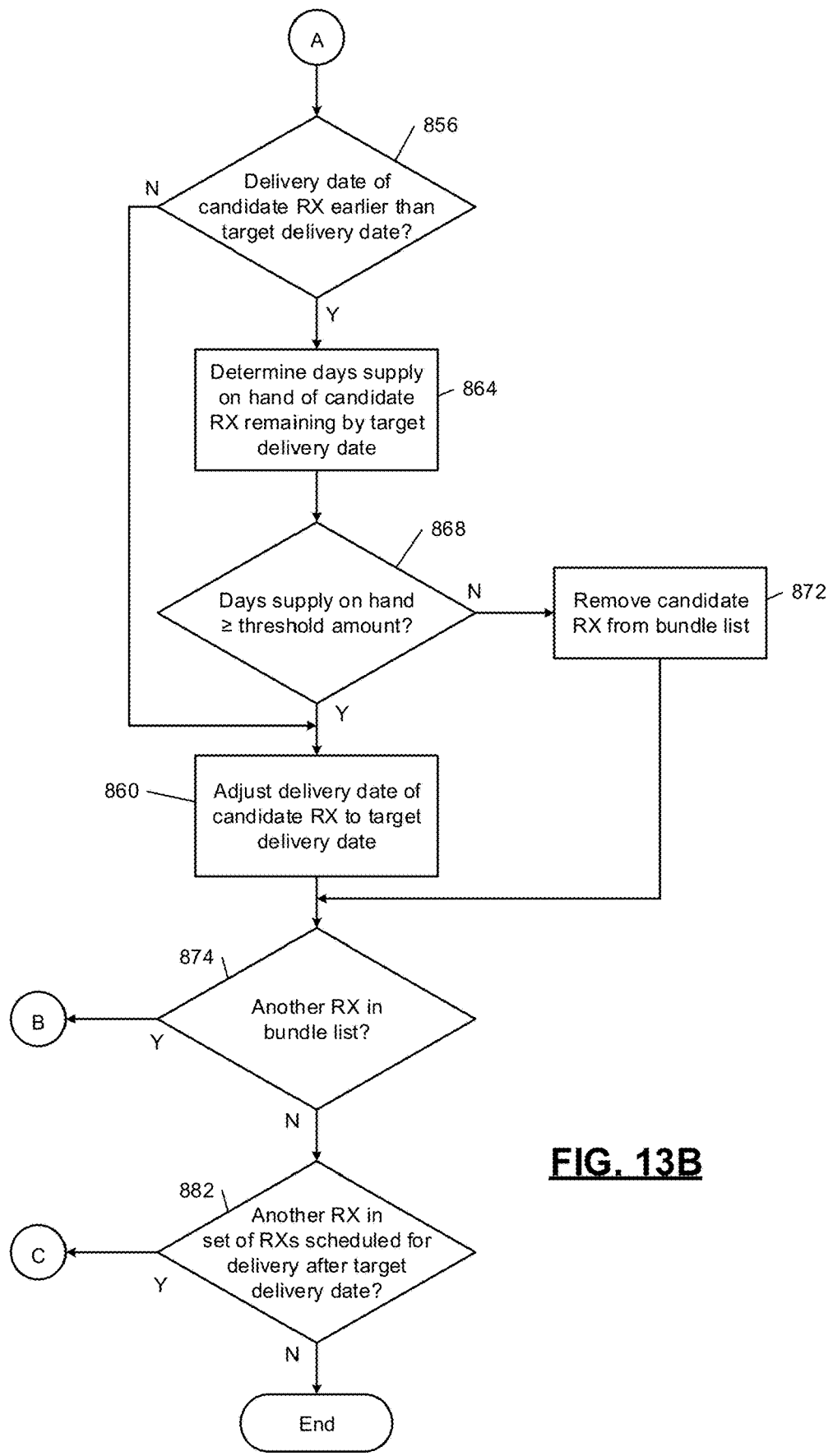

FIGS. 13A-13B together form a flowchart of example prescription delivery date bundling. Control begins upon receiving a bundle request. At 804, control obtains a set of prescriptions currently scheduled within a specified date range, such as one month from the present date. Control continues to 808, where control designates a prescription within the set of prescriptions that has the earliest scheduled delivery date as an anchor prescription. Control continues to 812 and sets a target delivery date to a scheduled delivery date of the anchor prescription. Then, at 816, control determines whether additional prescription deliveries are scheduled within a predetermined time of the target delivery date. For example, the predetermined time may be one week. In other words, when the predetermined time is one week, control determines whether additional prescription deliveries are scheduled within one week prior to and one week subsequent to the target delivery date.

If no additional prescription deliveries are scheduled within the predetermined time, control proceeds to 820 to designate a prescription with the next scheduled delivery date after the target delivery date as the anchor prescription and returns to 812. The anchor prescription is updated if no additional prescription deliveries are scheduled within the predetermined time of the target delivery date because only prescriptions near one another are bundled, preventing control from attempting to bundle prescriptions that are months apart.

If, at 816, additional prescription deliveries are scheduled within the predetermined time, control proceeds to 824. At 824, control creates a bundle list including each prescription scheduled for delivery within the predetermined time of the target delivery date but excluding prescriptions on the target delivery date. The bundle list represents the scheduled prescriptions that control will attempt to adjust to the target delivery date.

Control proceeds to 828 to select a first prescription in the bundle list as a candidate prescription. At 832, control obtains prescription parameters for the candidate prescription. As mentioned previously, prescription parameters may be obtained from the pharmacy device 106 described in FIG. 1. Control continues to 836 to determine a required fill date to deliver the candidate prescription on the target delivery date. At 840, control determines if the required fill date is too close to a prior fill date. In certain circumstances (for example, according to insurance or drug regulations) certain prescriptions may be required to be filled a predetermined amount of days apart from one another.

Therefore, if the required fill date is too close to the prior fill date at 840, control proceeds to 844 to determine an earliest possible fill date of the candidate prescription. Then, control proceeds to 848 to determine a delivery date of the candidate prescription based on the earliest possible fill date. At 852, control sets the target delivery date to the determined delivery date. Therefore, if moving the candidate prescription to the target delivery date results in the candidate prescription being filled too early, control adjusts the target delivery date to the presently scheduled delivery date of the candidate prescription. This represents an attempt to bundle the prescriptions scheduled within a predetermined time of the candidate prescription to the presently scheduled delivery date of the candidate prescription. Control then returns to 824. Otherwise, if at 840 the required fill date is not too close to the prior fill date, control proceeds to 856 of FIG. 13B.

In FIG. 13B, at 856, control determines if the presently scheduled delivery date of the candidate prescription is earlier than the target delivery date. If so, control proceeds to 864; otherwise, control continues to 860. At 864, control determines a DSOH of the candidate prescription as of the target delivery date. At 868, if the determined DSOH of the candidate prescription is greater than or equal to the threshold amount, control proceeds to 860. Otherwise, if the DSOH is equal to or below the threshold amount, control proceeds to 872. At 872, control removes the candidate prescription from the bundle list and continues at 874.

At 860, control adjusts the presently scheduled delivery date of the candidate prescription to the target delivery date. Then, control proceeds to 874 to determine if another prescription is in the bundle list. If the bundle list includes another prescription, control returns to 878 in FIG. 13A; otherwise, if the bundle list does not include another prescription, control continues to 882. At 882, control determines if another prescription is in the set of prescriptions and scheduled for delivery after the target delivery date. If not, then control has already attempted to bundle all possible groups scheduled in the specified date range and control ends. Otherwise, if another prescription is in the set of prescriptions and is scheduled for delivery after the target delivery date, control returns to 820 in FIG. 13A.

Returning to FIG. 13A, at 820 control designates the prescription with the next scheduled delivery date after the target delivery date as the anchor prescription. Control then continues at 812. At 878, control selects the next prescription in the bundle list as the candidate prescription and continues at 832 to obtain the relevant prescription parameters.

Conclusion

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A system for generating dynamic user interfaces, the system comprising:
   memory hardware configured to store instructions; and
   processor hardware configured to execute the instructions, wherein the instructions include:
     generating an interactive graphical user interface (GUI) having a plurality of fields, each field corresponding to one of a plurality of dates,
     retrieving a scheduled delivery date for a recipient from a datastore of the memory hardware,
     generating a selectable user interface element at a first field of the plurality of fields, wherein the first field corresponds to the scheduled delivery date for the recipient,
     presenting the GUI to a user of a user device via a web portal; and
     in response to receiving, via the GUI, user input corresponding to the user dragging-and-dropping the selectable user interface element to a second field of the plurality of fields:
     based on an identifier of the recipient, retrieving, from the datastore, a stated duration of a prior fill and a prior fill date corresponding to receipt of the prior fill by the recipient,
     determining an adjusted delivery date based on the second field,
     calculating a supply measure of the prior fill remaining with the recipient based on the stated duration, the prior fill date, and the adjusted delivery date,
     in response to the supply measure being less than a threshold, outputting an error message to the GUI, and
     in response to the supply measure being greater than the threshold, automatically transforming the GUI by moving the selectable user interface element of the GUI to the second field and transmitting the adjusted delivery date to the datastore to replace the scheduled delivery date.

2. The system of claim 1 wherein the instructions include calculating an earliest possible delivery date for a refill prescription of the recipient in response to user input corresponding to the user selecting the selectable user interface element.

3. The system of claim 2 wherein the instructions include, in response to the adjusted delivery date being prior to the earliest possible delivery date:
   automatically transforming the GUI by moving the selectable user interface element of the GUI to a third field of the plurality of fields, wherein the third field corresponds to the earliest possible delivery date, and
transmitting the earliest possible delivery date to the datastore to replace the scheduled delivery date.

4. The system of claim 3 wherein the instructions include blocking out a set of fields of the GUI corresponding to dates prior to the earliest possible delivery date.

5. The system of claim 4 wherein the instructions include blocking out the set of fields by applying a visual indication to the set of fields.

6. The system of claim 5 wherein the visual indication includes removing color from the set of fields.

7. The system of claim 5 wherein the visual indication includes increasing transparency of date text associated with the set of fields.

8. The system of claim 5 wherein the visual indication includes applying a black fill to the set of fields.

9. The system of claim 5 wherein the visual indication includes applying a grey fill to the set of fields.

10. The system of claim 5 wherein the visual indication includes applying a hatched pattern to the set of fields.

11. A computerized method for generating dynamic user interfaces, the computerized method comprising:
  generating an interactive graphical user interface (GUI) having a plurality of fields, each field corresponding to one of a plurality of dates;
  retrieving a scheduled delivery date for a recipient from a datastore;
  generating a selectable user interface element at a first field of the plurality of fields, the first field corresponding o the scheduled delivery date for the recipient;
  presenting the GUI to a user on a user device via a web portal, and
  in response to receiving, via the GUI, user input corresponding to the user dragging-and-dropping the selectable user interface element to a second field of the plurality of fields:
    based on an identifier of the recipient, retrieving, from the datastore, a stated duration of a prior fill and a prior fill date corresponding to receipt of the prior fill by the recipient,
    determining an adjusted delivery date based on the second field,
    calculating a supply measure of the prior fill remaining with the recipient based on the stated duration, the prior fill date, and the adjusted delivery date,
    in response to the supply measure being less than a threshold, outputting an error message to the GUI, and
    in response to the supply measure being greater than the threshold, automatically transforming the GUI by moving the selectable user interface element of the GUI to the second field and transmitting the adjusted delivery date to the datastore to replace the scheduled delivery date.

12. The computerized method of claim 11 further comprising calculating an earliest possible delivery date for a refill prescription of the recipient in response to user input corresponding to the user selecting the selectable user interface element.

13. The computerized method of claim 12 further comprising, in response to the adjusted delivery date being prior to the earliest possible delivery date:
  automatically transforming the GUI by moving the selectable user interface element of the GUI to a third field of the plurality of fields, the third field corresponding to the earliest possible delivery date, and
  transmitting the earliest possible delivery date to the datastore to replace the scheduled delivery date.

14. The computerized method of claim 13 further comprising blocking out a set of fields of the GUI corresponding to dates prior to the earliest possible delivery date.

15. The computerized method of claim 14 further comprising blocking out the set of fields by applying a visual indication to the set of fields.

16. The computerized method of claim 15 wherein the visual indication includes removing color from the set of fields.

17. The computerized method of claim 15 wherein the visual indication includes increasing transparency of date text associated with the set of fields.

18. The computerized method of claim 15 wherein the visual indication includes applying a black fill to the set of fields.

19. The computerized method of claim 15 wherein the visual indication includes applying a grey fill to the set of fields.

20. The computerized method of claim 15 wherein the visual indication includes applying a hatched pattern to the set of fields.

* * * * *